United States Patent [19]

McCarthy

[11] Patent Number: 5,273,221
[45] Date of Patent: Dec. 28, 1993

[54] SHARPS DESTRUCTION AND DISPOSAL APPARATUS

[75] Inventor: Ronald J. McCarthy, Port Macquarie, Australia

[73] Assignee: Elotown Pty. Ltd., Australia

[21] Appl. No.: 887,120

[22] Filed: May 19, 1992

Related U.S. Application Data

[63] Continuation of Ser. No. 634,225, Dec. 28, 1990, abandoned.

[30] Foreign Application Priority Data

Jun. 28, 1988 [AU] Australia ............................... PI9032
Nov. 14, 1988 [AU] Australia ............................... PJ1453

[51] Int. Cl.[5] ...................... B02C 13/02; B02C 13/22
[52] U.S. Cl. ........................................ 241/99; 241/100; 241/243; 241/606; 206/366; 220/254; 220/326
[58] Field of Search .................. 241/99, 243, 100, 15, 241/21, 606; 206/366, 370; 220/908, 254, 91, 326, 322, 481; 248/312.1, 313; 588/259, 900, 261

[56] References Cited

U.S. PATENT DOCUMENTS

| | | |
|---|---|---|
| 3,151,814 | 10/1964 | Morgan et al. . |
| 3,322,355 | 5/1967 | Bryant . |
| 3,655,138 | 4/1972 | Luscombe . |
| 3,703,970 | 11/1972 | Benson ............................... 241/99 X |
| 3,750,966 | 8/1973 | Anderson . |
| 3,889,886 | 6/1975 | Spivey ................................ 241/99 X |
| 3,926,379 | 12/1975 | Dryden et al. .................... 241/99 X |
| 3,929,295 | 12/1975 | Montalbano ...................... 241/99 X |
| 3,946,953 | 3/1976 | Hato . |
| 3,958,765 | 5/1976 | Musselman . |
| 3,960,334 | 6/1976 | Wudyka . |
| 3,995,768 | 12/1976 | Montalbano et al. . |
| 4,143,823 | 3/1979 | Judson, Jr. . |
| 4,205,794 | 6/1980 | Horton et al. . |
| 4,344,646 | 8/1982 | Michel .............................. 220/326 X |
| 4,445,644 | 5/1984 | Lemke . |
| 4,494,652 | 1/1985 | Nelson et al. ...................... 206/366 |

(List continued on next page.)

FOREIGN PATENT DOCUMENTS

| | | |
|---|---|---|
| 230164 | 9/1960 | Australia . |
| B-87968/75 | 5/1979 | Australia . |
| B-77526/81 | 11/1985 | Australia . |
| B-52261/86 | 6/1988 | Australia . |
| B-39295/85 | 9/1989 | Australia . |
| A-42479/89 | 2/1990 | Australia . |
| 0080882 | 6/1983 | European Pat. Off. . |
| 0267776 | 5/1988 | European Pat. Off. . |
| WO88/03416 | 3/1988 | PCT Int'l Appl. . |
| 1302851 | 1/1973 | United Kingdom . |

Primary Examiner—Mark Rosenbaum
Assistant Examiner—Frances Chin
Attorney, Agent, or Firm—Hill, Steadman & Simpson

[57] ABSTRACT

The present invention relates to an apparatus and method for safe disposal of hypodermic syringes, needles and other small, contaminated instruments such as, for example, scalpel blades, stitch cutters etc. (Commonly referred to as "sharps"). The apparatus firstly comprises a collection container having a primary lid which is movable between an open position and a closed position and is releasable latched in the closed position. The latch mechanism is adapted to be released when the contain is brought into cooperation with a destructor apparatus. The destructor apparats comprised a disposal receptacle adapted to receive the container and unlatch the lid, and a destructor means. adapted to generally comminute the material deposited therein. The destructor apparatus has an inlet and an outlet, a plurality of rotating blades which cooperate with two cutting plates which are arranged to define a flow path for the material between the inlet and the outlet. The cutting blades and the cutting plates cooperate to comminute the material by impact and cutting action. The present invention provides a convenient means of disposing of sharps generally without risk to the person handling the sharps.

22 Claims, 8 Drawing Sheets

U.S. PATENT DOCUMENTS

| | | |
|---|---|---|
| 4,531,437 | 7/1985 | Szablak et al. . |
| 4,580,688 | 4/1986 | Harris et al. . |
| 4,618,103 | 10/1986 | Wilson et al. . |
| 4,619,409 | 10/1986 | Harper et al. . |
| 4,637,545 | 1/1987 | Stewart .......................... 206/370 X |
| 4,657,139 | 4/1987 | Hanifl . |
| 4,670,227 | 6/1987 | Smith ............................. 588/900 X |
| 4,715,498 | 12/1987 | Hanifl ................................ 206/366 |
| 4,809,850 | 3/1989 | Laible et al. ......................... 206/366 |
| 4,809,915 | 3/1989 | Koffsky et al. . |
| 4,874,103 | 10/1989 | Quisenberry et al. .......... 220/908 X |
| 4,884,756 | 12/1989 | Pearson . |
| 4,889,290 | 12/1989 | Koffsky et al. . |
| 4,890,733 | 1/1990 | Anderson ........................ 220/908 X |
| 4,911,294 | 3/1990 | Russo et al. ........................ 206/366 |
| 4,913,309 | 4/1990 | Fink ................................ 220/254 X |
| 4,971,261 | 11/1990 | Solomons . |
| 4,979,683 | 12/1990 | Busdeker . |
| 5,033,634 | 7/1991 | Batchelor et al. .............. 220/326 X |
| 5,035,367 | 7/1991 | Nojima . |
| 5,054,696 | 10/1991 | Mennel et al. . |
| 5,064,124 | 11/1991 | Chang . |

SHARPS DESTRUCTION AND DISPOSAL APPARATUS

CROSS-REFERENCE TO RELATED APPLICATIONS

This application is a continuation of application Ser. No. 07/634,225, filed Dec. 28, 1990, and now abandoned.

TECHNICAL FIELD

The present invention relates to the safe disposal of hypodermic syringes, needles and other small, contaminated instruments such as, for example, scalpels blades, stitch cutters, etc. (commonly referred to as "sharps").

BACKGROUND ART

It is necessary to safely dispose of contaminated medical tools and other materials used in the medical environment. Such tools and the materials (i.e. sharps), or more specifically disposable, percutaneous devices, have been used, they must be safely disposed of so as to avoid reuse or accidental physical contact (e.g. needle stick injury).

One present known method of disposing of the above mentioned contaminated materials is to place the used syringe and needle into an apparatus which merely cuts the needle (sharp) from the syringe. The needle is kept in a container portion of the apparatus for later disposal, and the syringe portion is disposed of separately.

Alternatively, in large hospitals, medical centers and pathology departments, the whole needle (sharp) and syringe is placed in any one of a variety of containers as a complete unit, along with other contaminated medical tools or instruments. These containers are then disposed of by either incineration or burial at local garbage tips. Incineration of complete syringe is difficult and often incomplete after considerable incineration time. Further, the sharps and other instruments normally collected for disposal are usually (70–80%) highly infectious, and may remain infectious for a considerable time even after burial.

The first mentioned known method of disposal is awkward and requires the person disposing of the syringe to dispose of the syringe portions separately to that of the needle (sharp). The second above mentioned method of disposal requires the complete syringe and needle unit to be disposed of in one piece. Syringe and needle units are relatively bulky, and when a large number require disposal, the volume thereof can be inconveniently large.

OBJECTS OF INVENTION

It is the object of the present invention to provide apparatus which enables convenient collection of the sharps, a means of transferring the sharps into a sharps destruction apparatus which comminutes and sterilizes the sharps into a generally harmless state suitable for easy disposal by incineration or burial. A method is also defined.

DISCLOSURE OF THE INVENTION

In one broad form the present invention provides apparatus for destruction of contaminated materials such as sharps, comprising:
a sharps collection container having a primary opening and a primary lid adapted to close the primary opening in said container, said primary lid being movable with respect to the container between a closed position closing the primary opening, and an open position opening the primary opening;
said container further comprising a latch means adapted to retain the primary lid in the closed position, and to automatically release the primary lid when said container is brought into cooperation with a disposal receptacle of a destructor apparatus which is adapted to the latch means.

Another broad form of the present invention provides destructor apparatus having a sharps destructor which comprises;
a generally cylindrical chamber; a driven rotating cutter apparatus comprising a shaft rotatably mounted in said chamber and having a plurality of cutter blades mounted at predetermined positons along said shaft so as to rotate therewith;
at least one cutter plate mounted in said chamber and having a plurality of elongate slots of predetermined width; said cutter blades being generally aligned with respective slots in said plates and disposed to sweep therethrough;
an inlet located above said plates;
and an outlet located below said plate;
said plate being downwardly inclined from the inlet towards the outlet.

Preferably the apparatus comprises a disposal receptacle adapted to receive the container and having a projection disposed to operate the latch means of the container.

Another broad form of the present invention provides a method of disposing of contaminated medical tools, sharps and other materials, comprising:
collecting said materials in a collection container by inserting same through a primary opening in said container which is closable by a primary lid;
closing the primary opening with said primary lid which is detachably securable by a latch means into a closed position;
inverting and inserting said container in a disposal receptacle of a destructor apparatus which is adapted to release said latch mean whereby said primary lid is caused to open and discharge said material into said apparatus.

BRIEF DESCRIPTION OF THE DRAWINGS

Preferred forms of the present invention will now be described by way of example with reference the accompanying drawings, wherein.

BEST MODE FOR CARRYING OUT THE INVENTION

Figure 1:
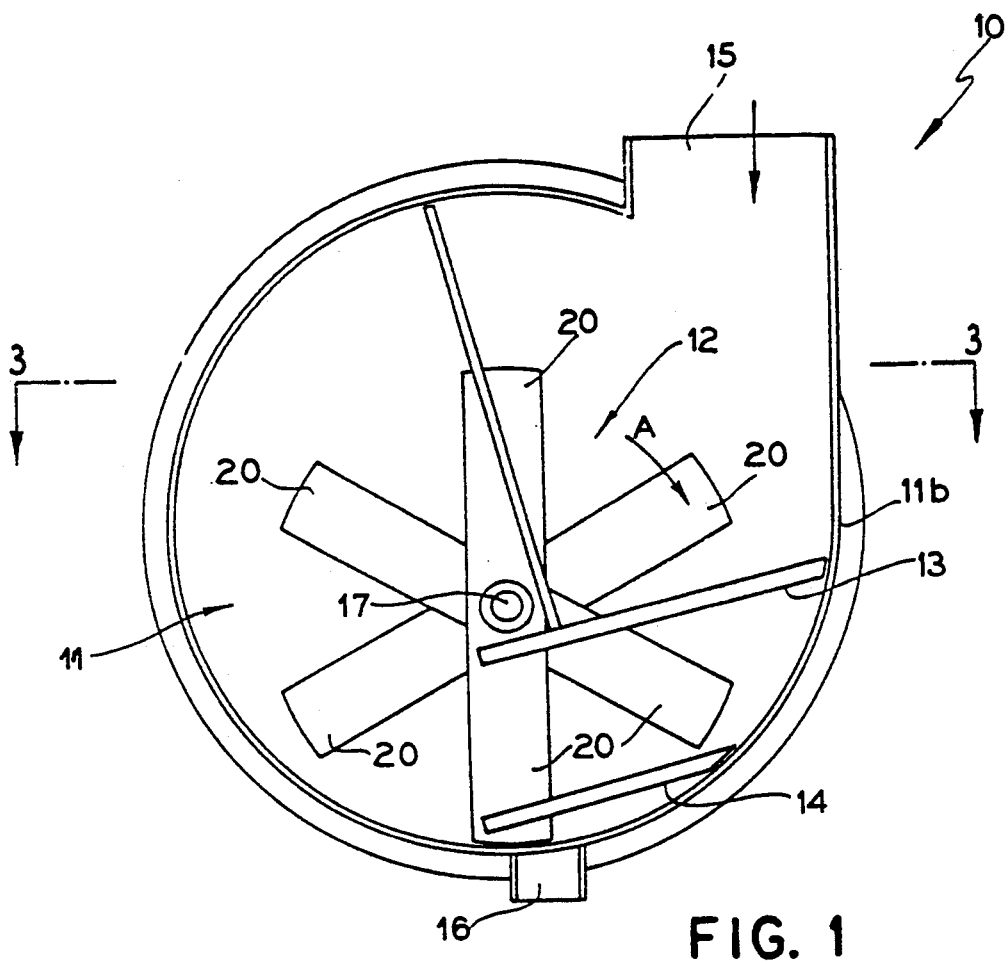
FIG. 1 is a schematic cross-sectional view of the sharps destructor apparatus.
Figure 3:
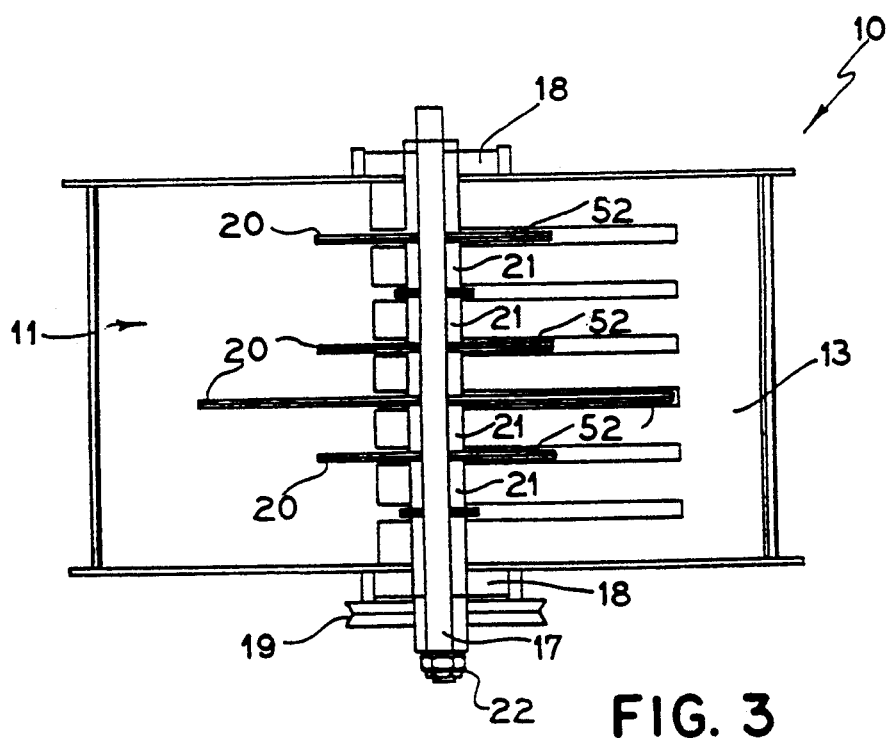
FIG. 3 is a schematic longitudinal sectional top plane view of the apparatus taken on line III—III of FIG. 1.
Figure 2:
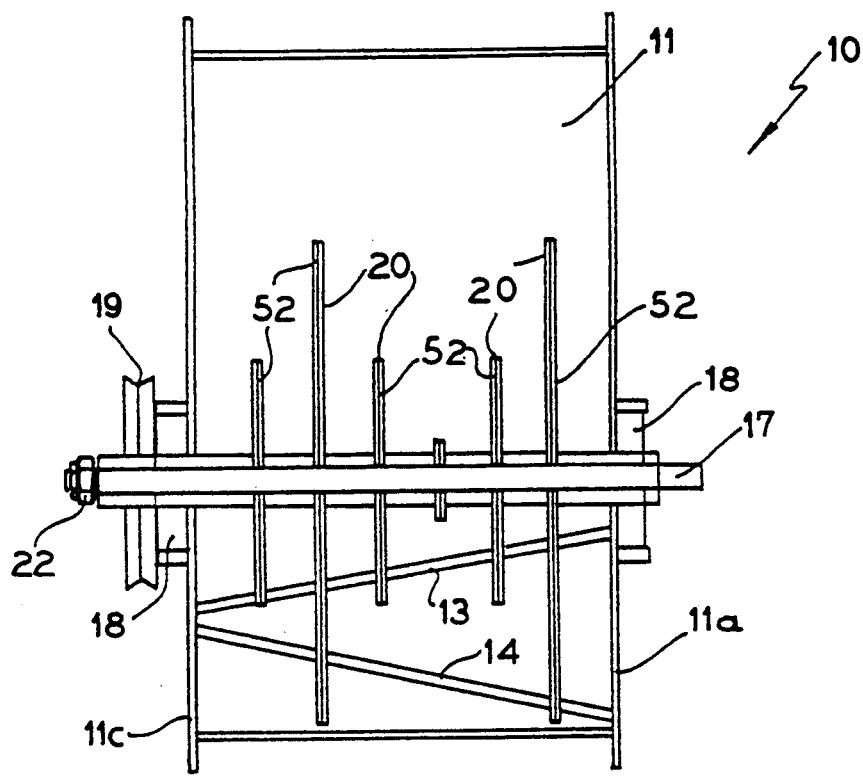
FIG. 2 is a longitudinal side elevation sectional view of the apparatus of FIG. 1.
Figure 4:
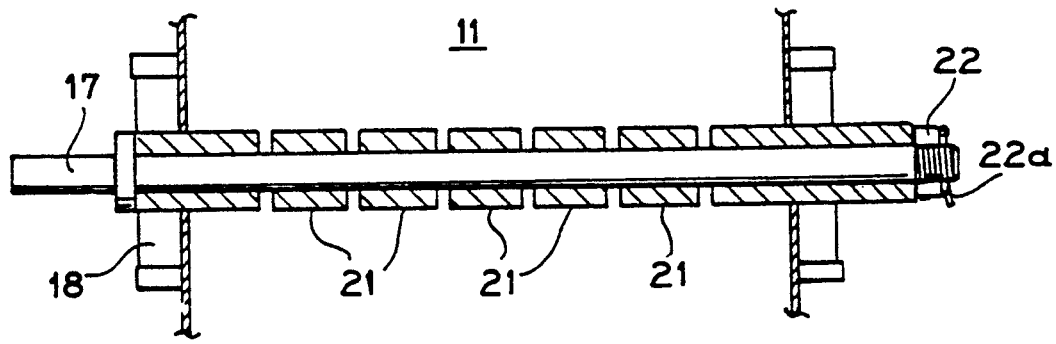
FIG. 4 is a longitudinal sectional view of the rotating cutter means of the destructor apparatus.
Figure 5:
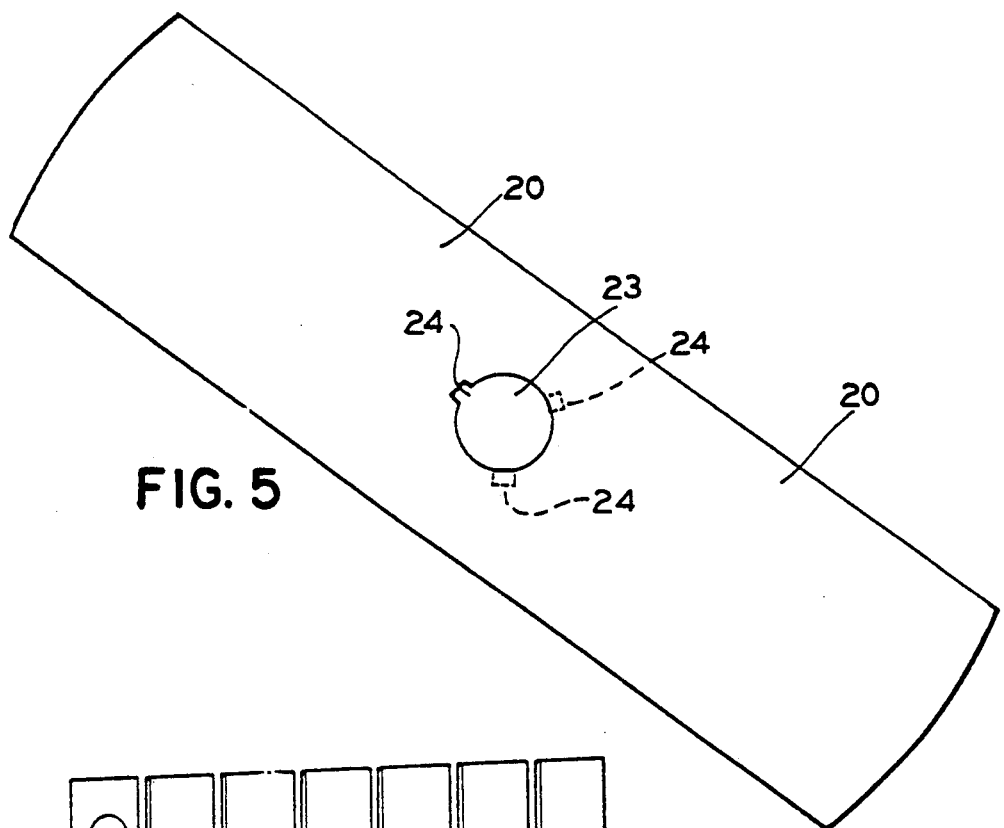
FIG. 5 is a top plane view of a cutter blade of the destructor apparatus.
Figure 6:
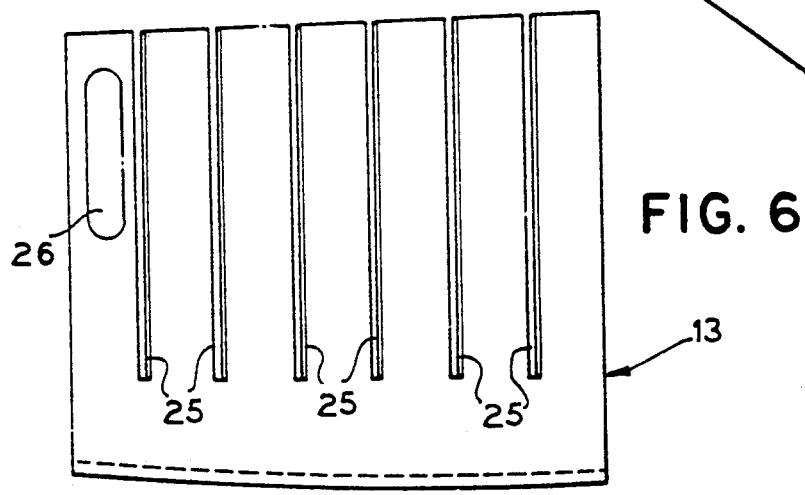
FIG. 6 is a top plane view of the upper cutter plate of the destructor apparatus.
Figure 7:
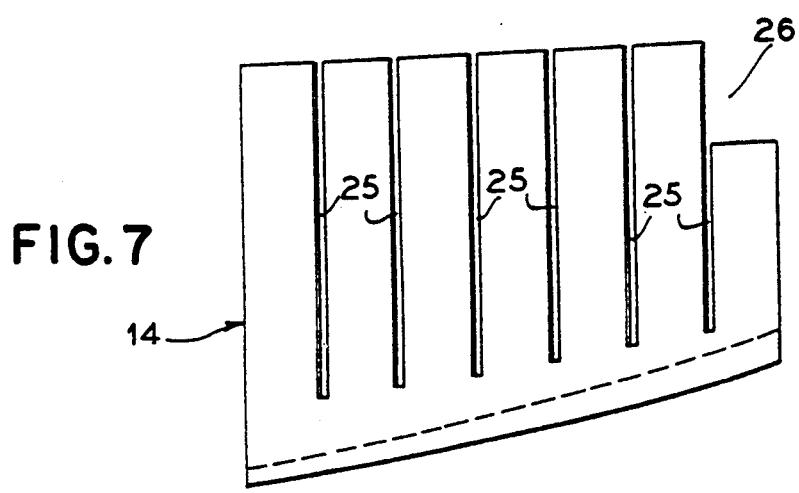
FIG. 7 is a top plane view of the lower cutter plate of the destructor apparatus.

In FIGS. 1 to 7 there is depicted sharps destructor apparatus 10 comprising a generally cylindrical chamber 11, a cutter means 12, an upper cutter plate 13 and a lower cutter plate 14. The chamber 11 comprises an inlet 15 located above the cutter means 12, and an outlet 16 located below the cutter means 12.

The cutter means 12 comprises a shaft 17 disposed generally parallel to the longitudinal axis of the cylindrical chamber 11, and rotatably mounted thereto by carrier bearing assemblies 18 which are fixed to the outside of the cylindrical chamber 11.

The shaft 17 projects to one side the cylindrical chamber 11 and has a pulley 19 fitted thereto to be driven by a vee belt drive from an electric motor (not shown) located within the housing 50.

A plurality of cutter blades 20 are mounted along the shaft 17 at predetermined intervals. The cutting blades 20 are fitted to and held in place by collars 21, and a square key provided on the shaft 17 engages key-ways 24 in the collars 21 and blades 20. The collars 21 and blades 20 are clamped together using a castellated nut 22 which is locked into position with split-pin 22a.

Each of the blades are provided with a central aperture 23 to receive the shaft 17, and a square key way 24 adapted to receive the square key the shaft 17. There are provided three types of blades 20, each respectively having the key way 24 orientated approximately 120° angularly away from that of the other two blades 20. Each of the three types of blades 20 are positioned sequentially along the shaft so that each respective blade 20 extends in a direction 120° angularly displaced from the adjacent blade 20. The preferred embodiment depicted in the drawings Is provided with six cutting blades 20. The blades 20 are approximately 10 mm thick and are provided with a central groove 52 extending along the cutting edges 51.

The upper cutting plate 13 and lower cutting plate 14 are each provided with six slots 25 and when they are fitted in the chamber in the specified positions, the slots 25 are generally aligned with the cutting blades 20, which sweep and pass through the slots 25 when the shaft 17 is rotated.

The inlet 15 of the chamber 11 is provided proximate one end 11a and to one side 11b of the chamber 11. The upper cutter plate 13, in cross-section, is inclined downwards from the side 11b towards the central vertical plane of the chamber 11, and in longitudinal section, is inclined downwards from the end 11a to the other end 11c of the chamber.

The lower cutter plate 14, in cross-section, is inclined downwards from side 11b, and in longitudinal section, is inclined downwards from the other end 11c to the end 11a of the chamber.

The lower cutter plate 14 is superposed under the upper cutter plate 13. The lowermost portion of each of the upper cutter plate 13 and the lower cutter plate 14 defined a recess 26 to allow the cut particles to fall therethrough due to gravity into a disposal bin.

Each of the cutter blades 20 cooperates with a respective slot 25 in each of the upper cutter plate 13 and lower cutter plate 14, whereby the width of the slots 25, and the clearance between the blades 20 and the slots 25 is predetermined so that the sharps entering the chamber 11 are generally comminuted due to impact and cutting action between the blades 20 and slots 25.

The chamber 11 is generally cylindrical and the shaft 17 is parallel to the walls of the chamber 11, and vertically aligned with the longitudinal axis of the chamber 11. The shaft 17 is spaced from the bottom surface of the chamber 11 a distance slightly more than the radius of the blades 20. The internal diameter of the cylindrical chamber 11 is approximately one and one half times greater than the diameter of each blade 20.

Each cutter plate 13, 14 is downwardly inclined approximately 15° from the horizontal in a direction from the same side surface 11b of the chamber 11 to a point just past the central vertical plane 1 of the chamber 11. The shaft 7 rotates in a direction whereby the blades approach each of the cutter plates from above (as shown by arrow "A").

The longitudinal downward inclination of each of the cutter plates 13, 14 is approximately 10° from the horizontal. This allows larger cut particles to move across the plate (13 or 14) by gravity to the respective recesses 26.

In operation, the apparatus 10 reduces hypodermic syringes, needles and other small contaminated instruments such as scalpels blades, stitch cutters, by impact and cutting to a proportionately smaller volume, thus facilitating easier transportation, storage and subsequent disposal or incineration. The above mentioned materials are put into the apparatus 10 via the inlet 15, and will exit therefrom via outlet 16 after the materials have passed along the upper and lower plates 13, 14.

The apparatus 10 reduces the volume of the material to be disposed of, and reduces the likelihood of physical contact with any of the contaminated materials.

Figure 8:
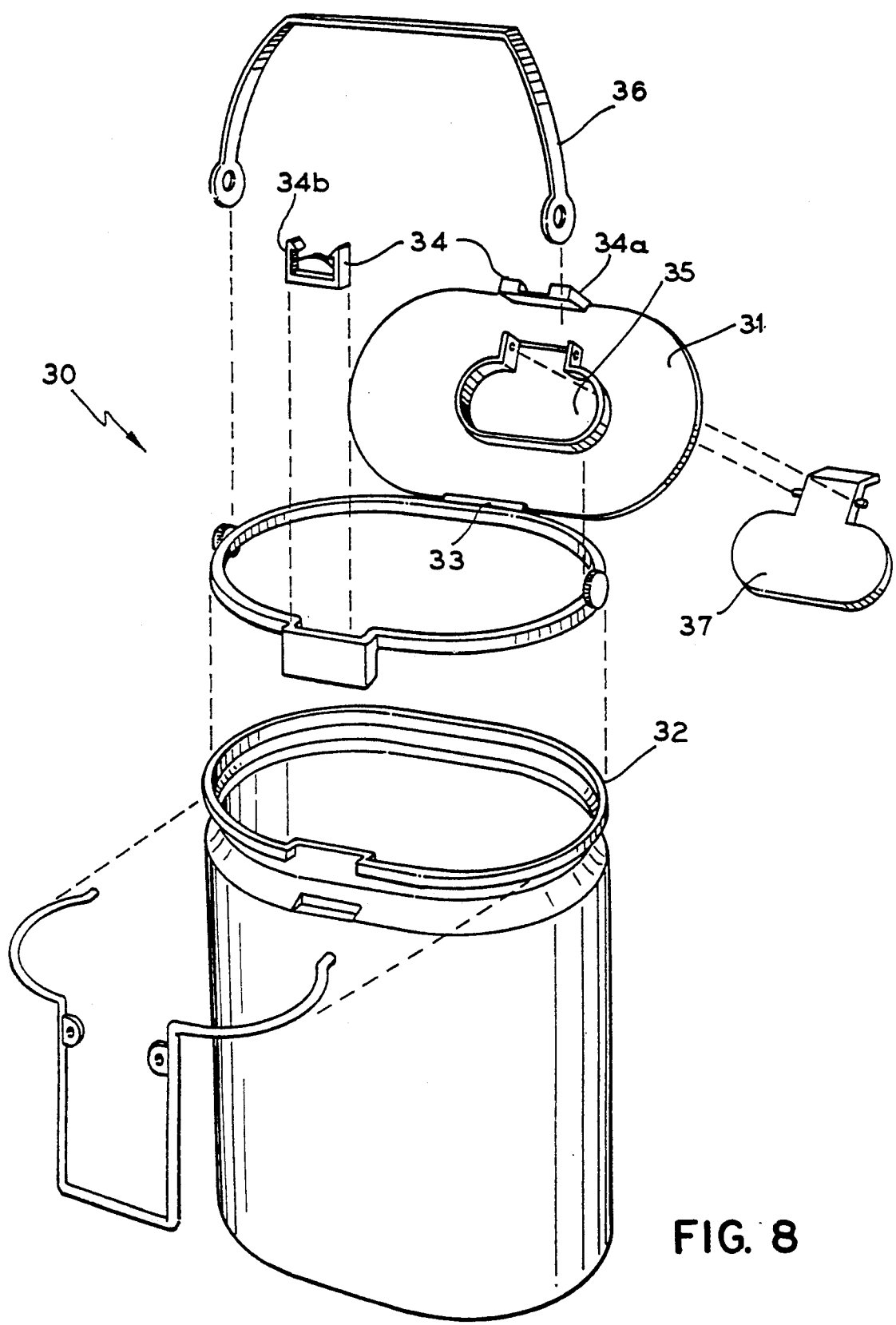
FIG. 8 is a schematic perspective exploded view of the sharps collection bin.
Figure 9:
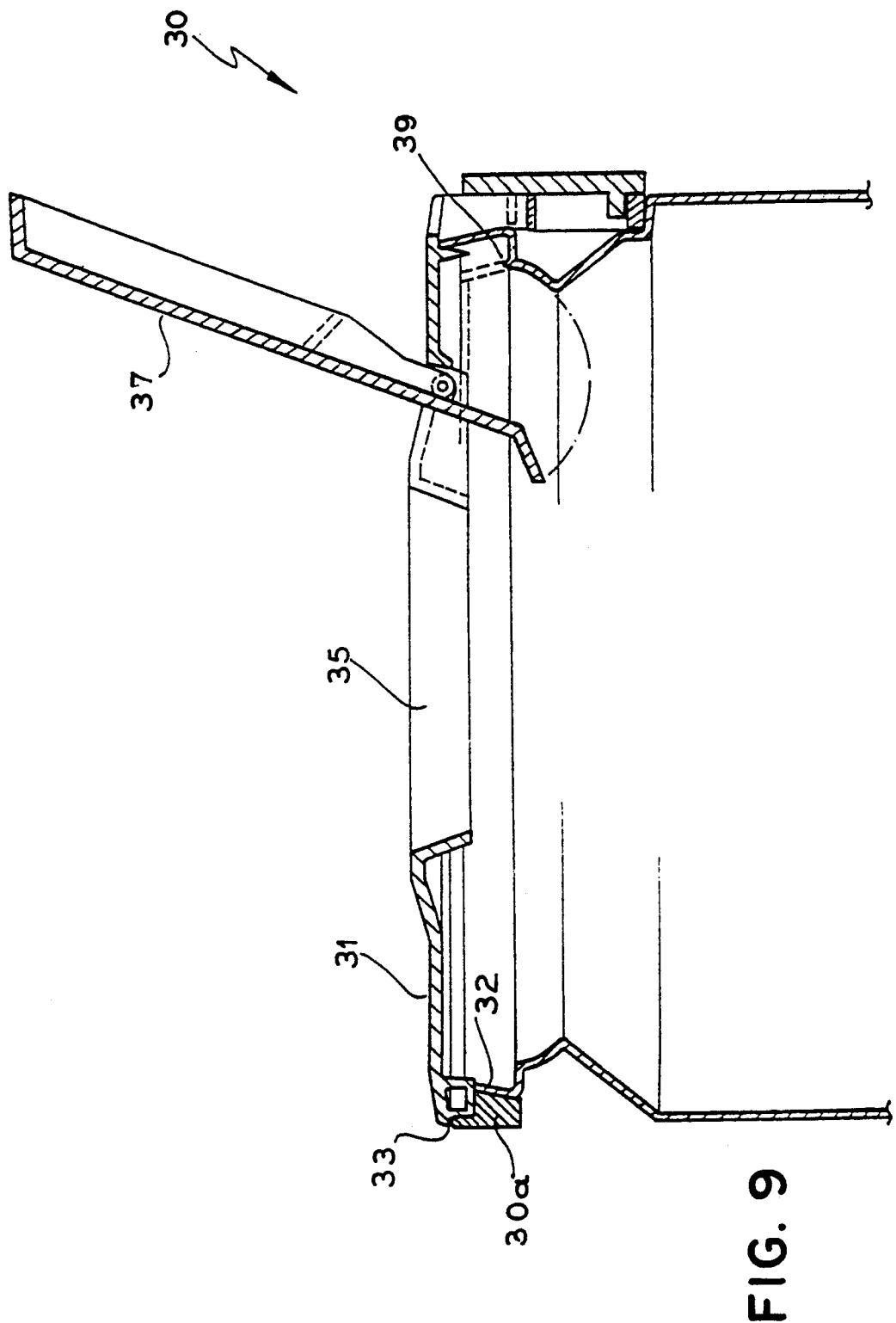
FIG. 9 is a cross-sectional view of the lid portion of the collection bin.

In FIGS. 8 and 9 is depicted a sharps collection container 30 being a generally open-ended bucket-shape, with a pivotable lid 31 mounted to a top edge 32 of the container 30 with a hinge 33. The container 30 is provided with a latch mechanism 34 which includes a striker member 34a on the lid 31 to engage a latch 34b on the container, adapted to detachably retain the primary lid 31 in a closed position closing the open end of the container 30. The primary lid 31 may be biased towards an open position extending transversely away from the plane of the opening, and towards the outside of the container 30.

The primary lid 31 is provided with a secondary lid 37 being pivotably mounted so as to be movable between a closed position closing an opening 35 in the primary lid 31, and an open position extending transversely away from the plane of the primary lid 31 outwards of the container 30. The secondary lid 37 is retained into the closed position by a resilient member 39. In the preferred embodiment the container 30 defines the resilient member 39. The retention may be overcome by additional force by the user to reopen the secondary lid 37.

The container 30 is further provided with a handle 36 for carrying purposes. The handle 36 is pivotable with respect to the container 30 between a retracted position and a carrying position.

The container 30 also comprises an inwardly projecting ridge 30a on the inside surface thereof proximate the opening. This ridge generally prevents contaminated fluids from being discharged from the container if accidentally knocked over.

Figure 10:
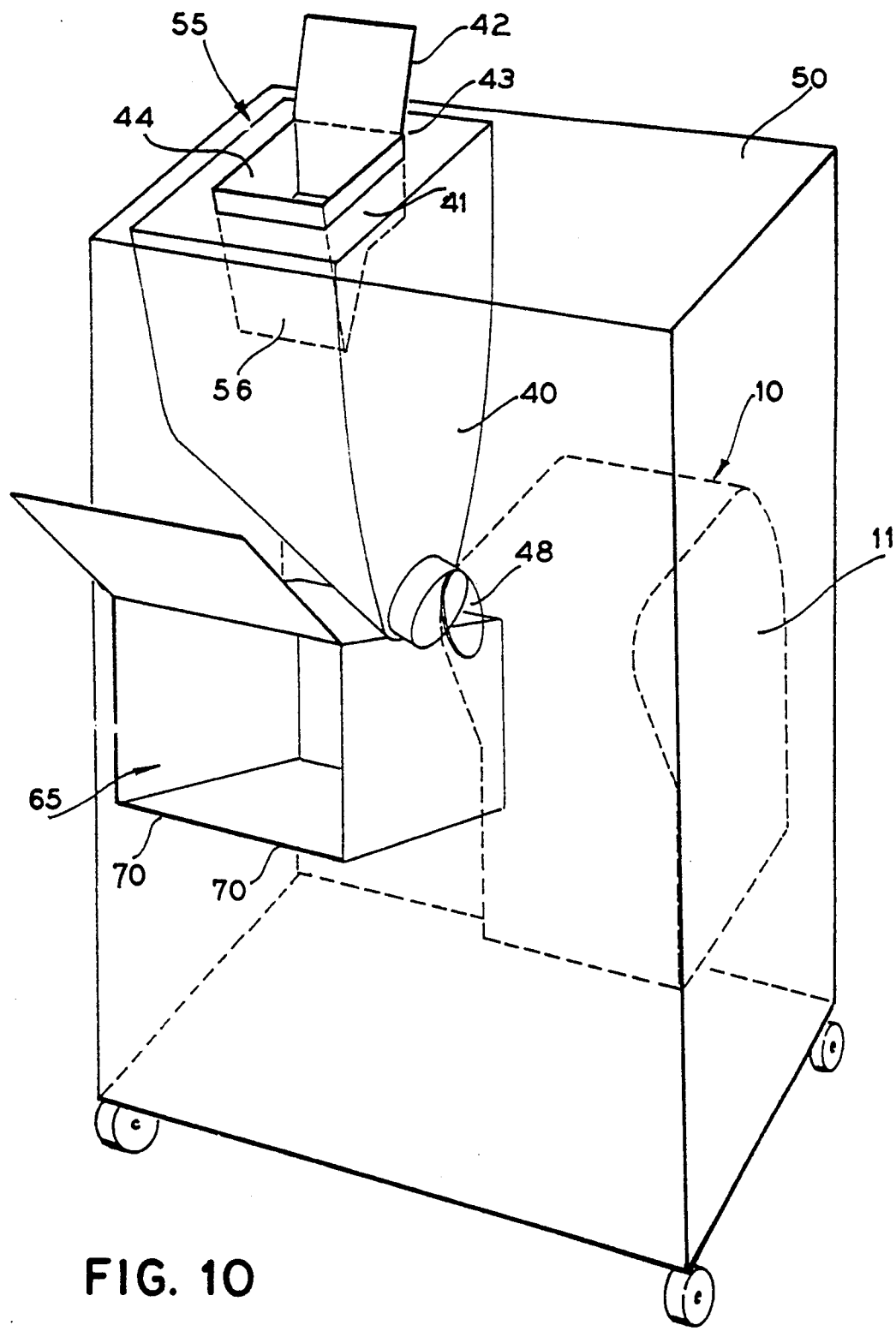
FIG. 10 is a schematic perspective view of the housing showing the disposal receptacle and washing receptacle.
Figure 11:
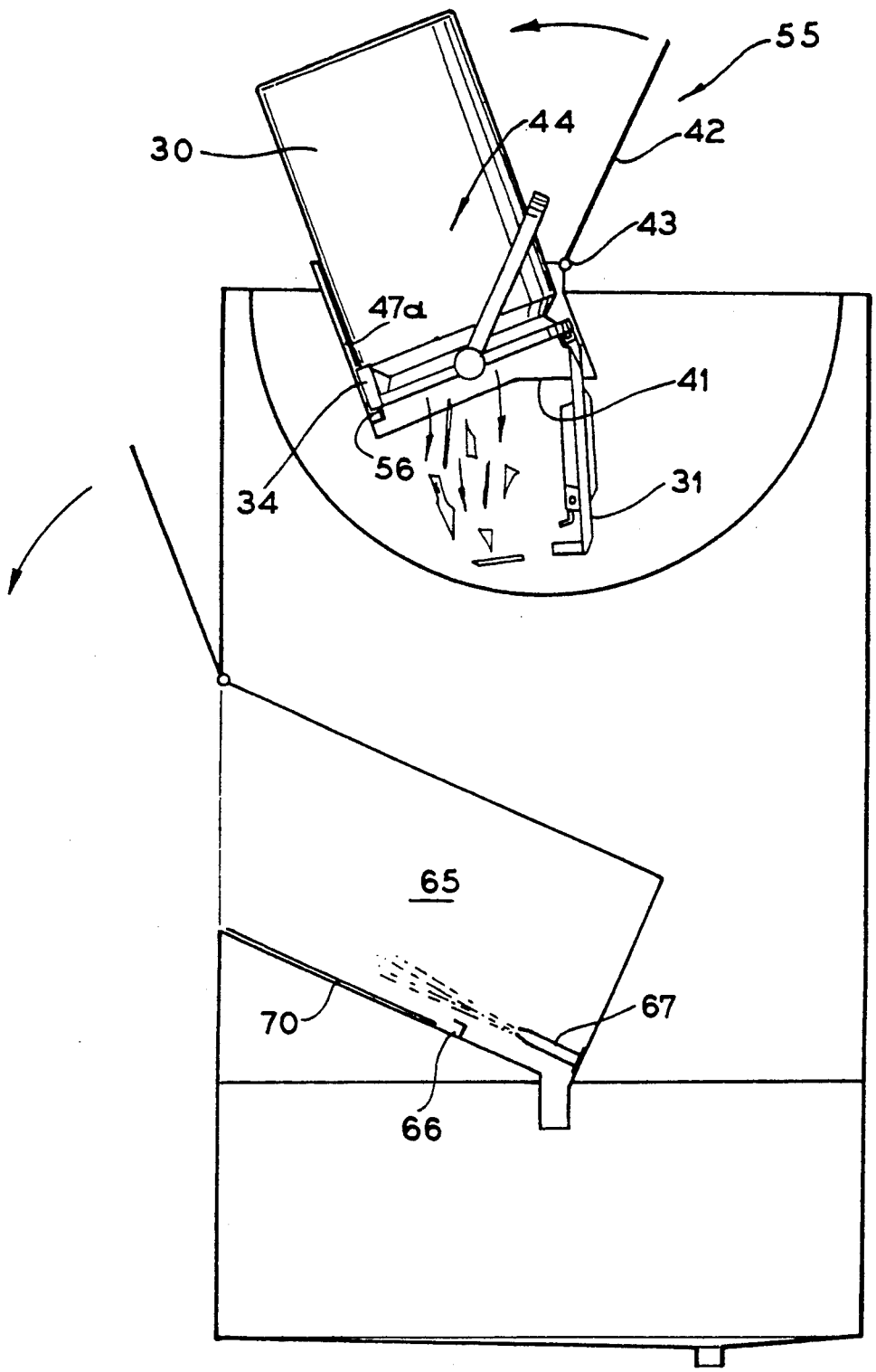
FIG. 11 is a cross sectional view of the housing of FIG. 10 with the disposal receptacle receiving a reusable sharps container.
Figure 12:
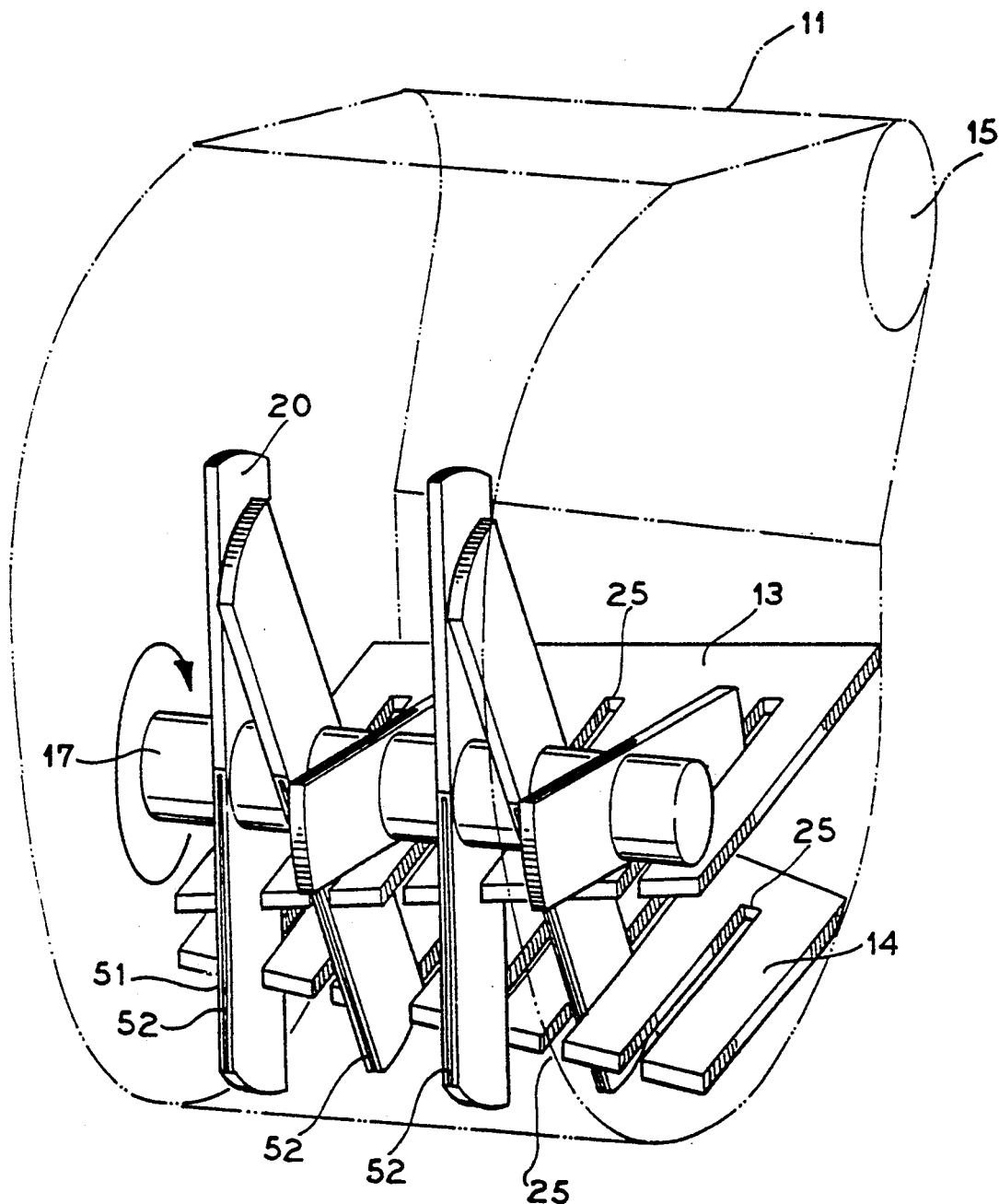
FIG. 12 is a schematic perspective view of the destructor chamber.

In FIG. 10 there is depicted a bulk bin 40 within the housing 50 having a bottom opening 41 which communicates with the inlet 15 of the destructor apparatus 10.

The bulk bin portion 40 is provided with a lid 42 pivotably attached along a pivotal axis 43 on the housing 50. The lid 42 is pivotable between a closed position closing an upper opening 44 in the housing 50, and an open position allowing the container 30 to be inserted in the disposal receptacle 55.

The disposal receptacle 55 comprises a opening 44 communicating with the inside of the bin 40.

The receptacle 55 further comprises a locating means 47 in the form of two slide guides 47a to locate an inverted collection container 30 in the receptacle 55. The lid 31 of the container 30 is caused to open when the container 30 is correctly positioned in the receptacle 55. That is, a latch release means 56 is provided in the receptacle 55 which is adapted to unlatch the latch mechanism 34, thereby allowing the lid 31 to move towards the open position and discharge the sharps directly into the bulk bin 40.

The bin 40 is also provided with a trap door 48 to control the discharge of the sharps into the inlet of the destructor apparatus 10. That is, the trap door 48 is operable so as to be openable only when the shaft 20 of the destructor apparatus 10 is rotating at the desired operating speed.

The bin 40 is also be provided with an agitator to maintain flow of the contaminated materials (sharps) through the bottom opening 41.

In use, the container 30 is used to collect the contaminated sharps by insertion through the secondary lid 37. When the container is full the secondary lid 37 is closed and the container may then be emptied into the bin 40 by inverting the container 30 and moving it into position in the receptacle 55 using the locating means 47. The latch release means 56 unlatches the latch mechanism 34 to release the contaminated sharps into the bulk bin 40 due to gravity. A number of container 30 loads of sharps may be deposited and stored in the bin 40 until it is desired to destroy and dispose of the contaminated sharps. The destructor apparatus 10 can then be operated by driving the shaft 20, and opening the trap door 48 of the bulk bin 40 whereby the sharps are caused to fall through the inlet 15 into the chamber 11. The sharps are then reduced by impact and cutting and discharged through the outlet 16. The material being discharged through the outlet 16 is generally safe, that is, the sharps are comminuted and do not pose a danger to the personnel who handle the material.

The comminuted contaminated materials are fed downwards through the chamber 11 to the bottom outlet 16, and collected in a sealable disposal bin 68 for subsequent disposal. The bins 68 may be disposed of by either incineration or burial at local garage tips.

The housing 50 further comprises a washing receptacle 65 adapted to slidably receive the container. The washing receptacle is similar to the discharge receptacle 55 in that a projection 66 is provided which is disposed to unlatch the latch means of the container therby allowing the primary lid to open. Washing jets 67 are provided which, selectively, direct sanitising fluid into the container. The washed container is then ready for reuse without risk of contaminated fluid being discharged therefrom when moved away from the housing 50.

Sanitising fluid is also introduced into the sharps either when they are being discharged from the container into the bulk bin 40, in the bulk bin 40 or within the chamber 11. This renders the comminuted material environmentally safe.

The comminuted material discharged from the apparatus 10 is able to be buried or incinerated. Previously, whole syringes were incinerated which took considerable time and energy, and was incomplete. That is, incineration leaves a relatively large volume of ashes. When the comminuted material of the present invention are incinerated, there is no residue and power requirements are substantially reduced.

The above described disposal apparatus is easy to use, and attends to the safety of staff and personnel whose job it is to handle the contaminated wastes on a daily basis.

I claim:

1. A system for collecting sharps and then destroying the collected sharps, said system comprising in combination at least one reusable sharps container; and a destructor apparatus having a disposal receptacle for receiving the reusable sharps container, each of said reusable sharps containers comprising a container having a primary opening, a primary lid being movably mounted with respect to the container and movable between a closed position closing the primary opening and an opened position opening the primary opening, latch means to retain the primary lid on the closed position in normal use and to automatically opening the primary lid when engaged by latch opening means of said disposal receptacle of said destructor apparatus when said container is inserted into said disposal receptacle, said primary lid having a secondary opening, a secondary lid being movably mounted on the primary lid and movable between a closed position closing the secondary opening and an opened position opening the secondary opening, said destructor apparatus, in addition to the disposal receptacle and latch opening means, comprising a chamber having an outlet and an inlet with the inlet being spaced above the outlet and in communication with said disposal receptacle, said chamber having cutter means for cutting sharps introduced through said inlet, said cutter means including a cutter plate being mounted in said chamber between the inlet and the outlet, said cutter plate having a plurality of elongated slots of a predetermined width being spaced along one edge, and a driven rotary cutter comprising a shaft being rotatably mounted in said chamber adjacent the one edge and having a plurality of cutter blades being mounted at predetermined positions along said shaft to be aligned with said slots of the cutter plate and to move through the slots as the shaft rotates, each cutter blade having a rectangular shape with cutting edges, said plate being inclined downward from the inlet toward the outlet so that the sharps are inserted into the container through the secondary opening but are removed through the primary opening when the container is inserted into the disposal receptacle and the latch opening means actuates the latch means to open the primary opening to discharge the sharps from the container to enter the inlet and move along the cutter plate to be repeatedly cut and impacted by the rotating cutter blades to be transformed into small pieces prior to exiting the outlet of the chamber.

2. A system according to claim 1, wherein the latch mean includes a striker member being mounted on one of the primary lid and the container and a latch being mounted on the other of said container and primary lid to releasably retain the striker member, said latch being openable by a straight projection of said latch opening means.

3. A system according to claim 1, wherein said cutter plate is downwardly inclined longitudinally in the chamber with a lower end having a discharge opening and the upper end being generally adjacent said inlet, said chamber including a second cutter plate being positioned under the first-mentioned cutter plate and being downwardly inclined longitudinally in the chamber with an upper end adjacent the discharge end of the first-mentioned cutter plate and the lower end having a discharge opening positioned above the outlet so that a sharp landing on said first-mentioned cutter plate moves along and is subjected to cutting and impact until it reaches the discharge opening to fall onto the second cutter plate where it is subjected to additional cutting and impact prior to being discharged through the outlet.

4. A destructor apparatus for destroying sharps comprising a chamber having an outlet and an inlet with the inlet being spaced above the outlet; said chamber having cutter means for destroying sharps introduced through said inlet; a disposal receptacle for receiving a reusable container, said disposal receptacle being in communication with said inlet of said chamber; said cutter means including a planar cutter plate and a driven rotary cutter, said cutter plate being mounted in said chamber between the inlet and the outlet, said cutter plate having a plurality of elongated slots of a predetermined width being spaced along one edge, said driven rotary cutter comprising a shaft being rotatably mounted in said chamber adjacent the one edge and having a plurality of cutter blades being mounted at predetermined positions along said shaft to be aligned with said slots of the cutter plate and to move through the slots as the shaft rotates, each cutter blade having a rectangular shape with cutting edges; said plate being in a downwardly inclined plane from the inlet toward the outlet so that a sharp entering the inlet moves along the plate and is repeatedly cut and impacted by the rotating cutter blades to be transformed into small pieces prior to exiting the outlet of the chamber.

5. An apparatus according to claim 4 wherein said disposal receptacle has a latch opening means disposed to operate latch means on the container as the container is inserted into the receptacle.

6. Apparatus as defined in claim 4 further washing means to wash the container with a sanitising fluid.

7. The apparatus of claim 4, wherein said disposal receptacle is in direct communication with said chamber.

8. An apparatus according to claim 4, wherein the cutting edges of said cuter blades are provided with grooves.

9. The apparatus of claim 4 wherein said blades are approximately 10 mm thick and have a longitudinal groove along a side edge thereof.

10. An apparatus according to claim 4, which includes a second cutter plate being generally positioned under the first-mentioned cutter plate, each of said cutter plates being downwardly inclined longitudinally of the chamber and defining a discharge opening at a lower end, said inlet being generally above an upper end of said first-mentioned cutter plate, an upper end of said second cutter plate being generally below the discharge opening of said first-mentioned cutter plate, and said outlet being generally below said discharge opening of the second cutter plate.

11. The apparatus of claim 10, wherein the longitudinal downwardly inclination of each of said plates is approximately 10° from the horizontal.

12. The apparatus of claim 10 wherein each of said plates are also downwardly inclined and extend from a side of said chamber at least to a central longitudinal vertical plane of the chamber.

13. The apparatus of claim 12 further includes a retaining plate extending upwards from a lower side of the first mentioned plate substantially to the roof of the chamber.

14. The apparatus of claim 12, wherein the downwardly inclination of each of said plates from a side of said chamber is approximately 15° from the horizontal.

15. A reusable sharps container comprising a container having a primary opening, a primary lid being movably mounted with respect to the container and movable between a closed position closing the primary opening and an opened position opening the primary opening, latch means to retain the primary lid in the closed position in normal use and to automatically open the primary lid when engaged by latch opening means of a disposal receptacle of an apparatus when said container is inserted into said disposal receptacle, said primary lid having a secondary opening, a secondary lid being movably mounted on the primary lid and movable between a closed position closing the secondary opening and an opened position opening the secondary opening, so that the sharps are inserted into the container through the secondary opening but are removed through the primary opening directly onto the disposal receptacle whereby the container is emptied and can be reused.

16. The container of claim 15 wherein said secondary lid is detachably retainable in said closed position by a resilient member.

17. The container of claim 15 further comprising a ridge provided on a inside surface thereof generally coextensive with and proximate the primary opening.

18. The container of claim 15 further comprising a carry handle.

19. The container of claim 15 further comprising a wall hanging member adapted to mount the container to a verticle support.

20. A reusable sharps container according to claim 15, wherein the primary lid is pivotably mounted on the container and the secondary lid is pivotably mounted on the primary lid.

21. The container of claim 15 wherein said latch means comprises a striker member being mounted on one of the primary lid and the container, and a latch being mounted on the other of said container and said lid to releasably retain the striker member, said latch being operable by a generally straight projection of said latch opening means.

22. The container of claim 21 wherein said latch comprises a hook portion adapted to resiliently deform and thereby retain said striker member, and to be resiliently deformed by said projection to release said striker member.

* * * * *

UNITED STATES PATENT AND TRADEMARK OFFICE
CERTIFICATE OF CORRECTION

PATENT NO. : 5,273,221
DATED : December 28, 1993
INVENTOR(S) : Ronald J. McCarthy It is certified that error appears in the above—identified patent and that said Letters Patent is hereby corrected as shown below:

Column 2, line 49, after "reference" insert --to--.

Column 3, line 37, after "key" insert --of--.

Column 4, line 42, after "9" insert --there--.

Column 6, line 32, change "on" to read --in--; and
line 33, change "opening" to read --open--.

Column 7, line 49, delete "a".

Signed and Sealed this

Second Day of April, 1996

Attest:

BRUCE LEHMAN

Attesting Officer

Commissioner of Patents and Trademarks